US00PP19840P2

(12) United States Plant Patent
Klemm

(10) Patent No.: US PP19,840 P2
(45) Date of Patent: Mar. 24, 2009

(54) *NIEREMBERGIA* PLANT NAMED 'KLENC06134'

(50) Latin Name: *Nierembergia caerulea*
Varietal Denomination: KLENC06134

(75) Inventor: Nils Klemm, Stuttgart (DE)

(73) Assignee: Klemm + Sohn GmbH + Co. Kg, Stuttgart (DE)

( * ) Notice: Subject to any disclaimer, the term of this patent is extended or adjusted under 35 U.S.C. 154(b) by 0 days.

(21) Appl. No.: 12/002,490

(22) Filed: Dec. 17, 2007

(51) Int. Cl.
*A01H 5/00* (2006.01)

(52) U.S. Cl. ..... Plt./459
(58) Field of Classification Search ..... Plt./459
See application file for complete search history.

*Primary Examiner*—Wendy C. Haas
(74) *Attorney, Agent, or Firm*—C. A. Whealy

(57) ABSTRACT

A new and distinct cultivar of *Nierembergia* plant named 'KLENC06134', characterized by its compact, upright and outwardly spreading and mounding plant habit; moderately vigorous growth habit; freely branching habit; large white-colored flowers; freely and continuous flowering habit; and good garden performance.

2 Drawing Sheets

Botanical designation: *Nierembergia caerulea.*
Cutlivar denomination: 'KLENC06134'.

BACKGROUND OF THE INVENTION

The present invention relates to a new and distinct cultivar of *Nierembergia,* botanically known as *Nierembergia caerulea* and hereinafter referred to by the name 'KLENC06134'.

The new *Nierembergia* is a product of a planned breeding program conducted by the Inventor in Stuttgart, Germany. The objective of the breeding program was to create new compact *Nierembergia* cultivars that flower continuously.

The new *Nierembergia* originated from an open-pollination during the summer of 2003, in Stuttgart, Germany, of a proprietary selection of *Nierembergia caerulea* identified as code number J 3, not patented, as the female, or seed, parent with an unknown selection of *Nierembergia caerulea,* as the male, or pollen, parent. The new *Nierembergia* was discovered and selected by the Inventor as a single flowering plant within the progeny of the stated open-pollination in a controlled environment in Stuttgart, Germany in May, 2004.

Asexual reproduction of the new *Nierembergia* by vegetative cuttings in a controlled environment in Stuttgart, Germany since May, 2004, has shown that the unique features of this new *Nierembergia* are stable and reproduced true to type in successive generations.

SUMMARY OF THE INVENTION

The cultivar KLENC06134 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'KLENC06134'. These characteristics in combination distinguish 'KLENC06134' as a new and distinct cultivar of *Nierembergia:*

1. Compact, upright to outwardly spreading and mounding plant habit.
2. Moderately vigorous growth habit.
3. Freely branching habit.
4. Large white-colored flowers.
5. Freely and continuous flowering habit.
6. Good garden performance.

Compared to plants of the female parent selection, plants of the new *Nierembergia* are more compact.

Plants of the new *Nierembergia* can also be compared to plants of the cultivar BeBop Blue, unpatented. In side-by-side comparisons conducted in Stuttgart, Germany, plants of the new *Nierembergia* and the cultivar BeBop Blue differed in the following characteristics:

1. Plants of the new *Nierembergia* were more compact than plants of the cultivar BeBop Blue.
2. Plants of the new *Nierembergia* flowered earlier than plants of the cultivar BeBop Blue.
3. Plants of the new *Nierembergia* and the cultivar BeBop Blue differed in flower color as plants of the cultivar BeBop Blue have blue-colored flowers.

BRIEF DESCRIPTION OF THE PHOTOGRAPHS

The accompanying colored photographs illustrate the overall appearance of the new *Nierembergia,* showing the colors as true as it is reasonably possible to obtain in colored reproductions of this type. Colors in the photographs may differ slightly from the color values cited in the detailed botanical description which accurately describe the colors of the new *Nierembergia.*

The photograph on the first sheet is a side perspective view of a typical flowering plant of 'KLENC06134' grown in a container.

The photograph on the second sheet is a close-up view of typical flowers of 'KLENC06134'.

DETAILED BOTANICAL DESCRIPTION

The aforementioned photographs and following observations, measurements and values describe plants grown in Stuttgart, Germany, under commercial practice during the spring in a glass-covered greenhouse with day temperatures ranging from 14° C. to 16° C., night temperatures ranging from 12° C. to 14° C. and light levels about 20,000 lux. Plants had been growing for about five months when the photographs and description were taken. In the following description, color references are made to The Royal Horticultural Society Colour Chart, 2001 Edition, except where general terms of ordinary dictionary significance are used.

Botanical classification: *Nierembergia caerulea* cultivar KLENC06134.

Parentage:

*Female, or seed, parent.*—Proprietary selection of *Nierembergia caerulea* identified as code number J 3, not patented.

*Male, or pollen, parent.*—Unknown selection of *Nierembergia caerulea,* not patented.

Propagation:

*Type.*—By vegetative cuttings.

*Time to initiate roots, summer.*—About three weeks at 20° C. to 26° C.

*Time to initiate roots, winter.*—About four weeks at 20° C.

*Time to produce a rooted young plant roots.*—About 25 days at 20° C.

*Root description.*—Fine, fibrous; white in color.

*Rooting habit.*—Freely branching; moderately dense.

Plant description:

*Plant form/habit.*—Compact, upright to outwardly spreading and mounding plant habit; moderately vigorous growth habit. Freely branching habit; about seven primary lateral branches with numerous secondary lateral branches developing per plant.

*Plant height.*—About 5 cm.

*Plant width* (*spread*).—About 18 cm.

*Lateral branches.*—Length: About 9 cm. Diameter: About 1 mm. Internode length: About 8 mm to 15 mm. Strength: Moderately strong. Texture: Smooth, glabrous. Color: 146B.

Foliage description:

*Arrangement.*—Alternate, simple; sessile.

*Length.*—About 5 mm to 10 cm.

*Width.*—About 2 mm.

*Shape.*—Lanceolate.

*Apex.*—Acute.

*Base.*—Cordate.

*Margin.*—Entire.

*Texture, upper and lower surfaces.*—Smooth, glabrous.

*Venation pattern.*—Pinnate.

*Color.*—Developing and fully expanded leaves, upper surface: 146A; venation, 146C. Developing and fully expanded leaves, lower surface: 146B; venation, 146C.

Flower description:

*Flower type/habit.*—Single salverform flowers; flowers face mostly upright. Freely flowering habit with about 50 flowers and flower buds developing per lateral branch.

*Fragrance.*—None detected.

*Natural flowering season.*—Continuously flowering from spring to late autumn in Stuttgart, Germany. Flowers not persistent.

*Postproduction longevity.*—Flowers last about five days on the plant.

*Flower buds.*—Height: About 1.3 cm. Diameter: About 4 mm. Shape: Obovate. Color: 154D.

*Flower diameter.*—About 2.5 cm.

*Flower depth.*—About 3 cm.

*Petals.*—Quantity per flower: Typically five in a single whorl; petals fused. Length: About 1.2 cm. Width: About 1 cm. Shape: Roughly spatulate. Apex: Obtuse to acute. Margin: Entire. Texture, upper and lower surfaces: Smooth, glabrous. Color: Developing and fully expanded petals, upper surface: 155B; towards the base, close to 9A. Developing and fully expanded petals, lower surface: 155D.

*Sepals.*—Quantity per flower: Typically five in a single whorl, fused at base; star-shaped calyx. Length: About 5 mm. Width: About 3 mm. Shape: Lanceolate. Apex: Acute. Margin: Entire. Texture, upper and lower surfaces: Smooth, glabrous. Color, upper and lower surfaces: 147A.

*Peduncles.*—Length: About 5 mm. Diameter: About 1 mm. Angle: About 30° from vertical. Texture: Smooth, glabrous. Color: 146A.

*Reproductive organs.*—Stamens: Quantity per flower: Typically five. Anther shape: Elliptic. Anther length: About 1 mm. Anther color: 5A. Pollen amount: Abundant. Pollen color: 5A. Pistils: Quantity per flower: One. Pistil length: About 2 cm. Stigma shape: Oval. Stigma color: 144A. Style color: 145C. Ovary color: 145C.

*Fruits.*—Length: About 3 mm. Diameter: About 3 mm. Texture: Smooth. Color: 165B.

*Seeds.*—Quantity per fruit: About 15. Length: About 1 mm. Diameter: About 1 mm. Texture: Smooth. Color: 200C.

Disease/pest resistance: Plants of the new *Nierembergia* have not been noted to be resistant to pathogens and pests common to *Nierembergia.*

Garden performance: Plants of the new *Nierembergia* have been observed to have good garden performance and tolerate rain, wind and temperatures from about 1° C. to about 40° C.

It is claimed:

1. A new and distinct *Nierembergia* plant named 'KLENC06134' as illustrated and described.

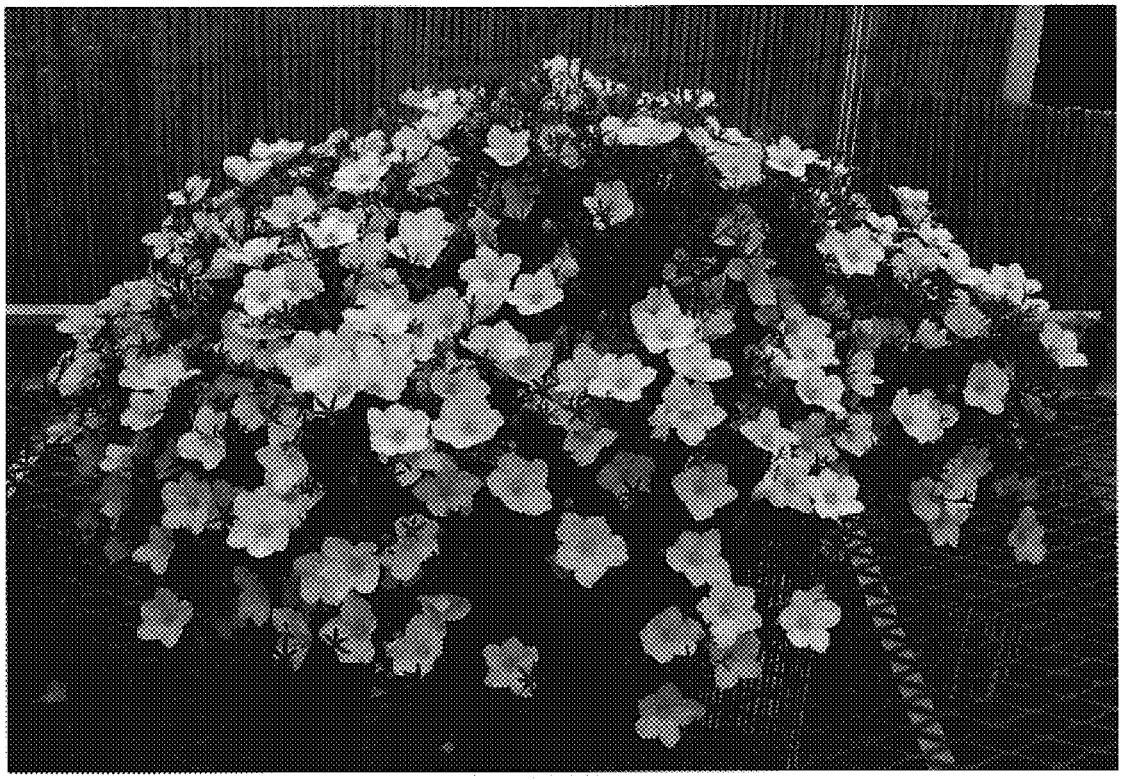

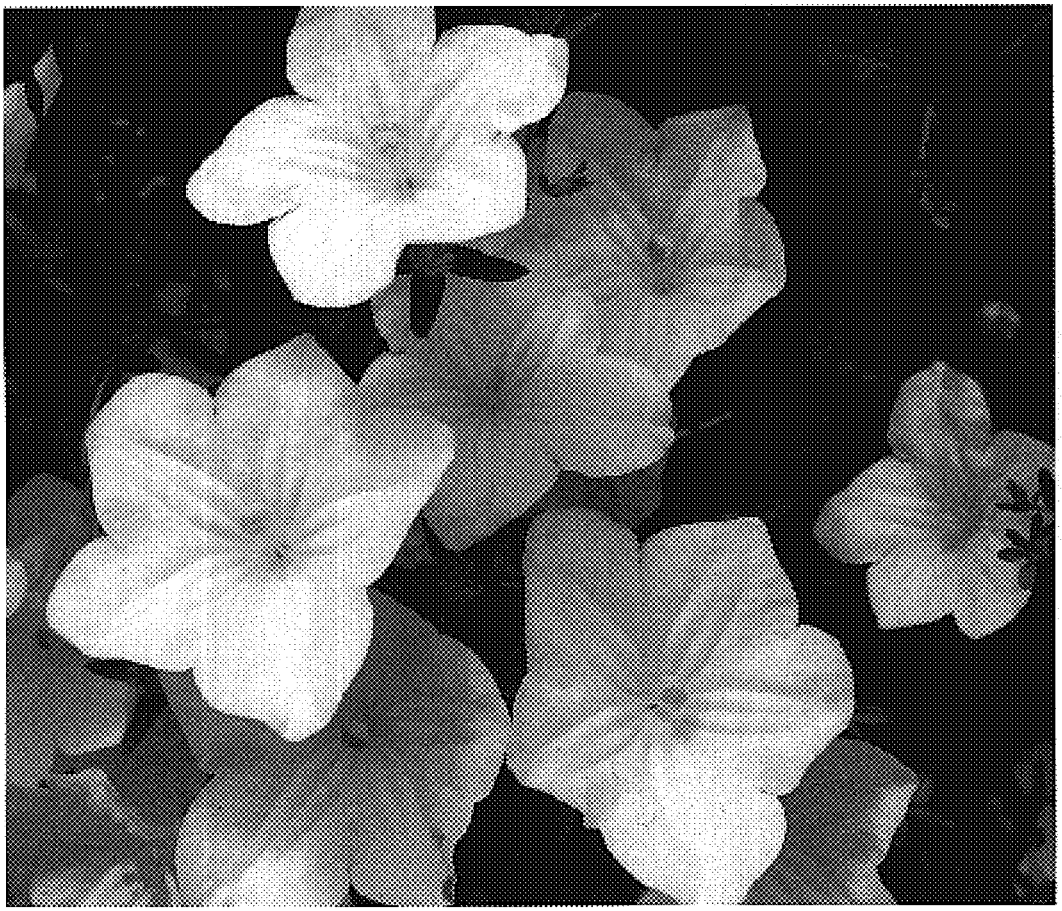

* * * * *